United States Patent
Harris et al.

(10) Patent No.: US 9,060,865 B2
(45) Date of Patent: *Jun. 23, 2015

(54) MONOPOLAR CONSTRAINED ACETABULAR COMPONENT

(71) Applicant: The General Hospital Corporation, Boston, MA (US)

(72) Inventors: William H. Harris, Belmont, MA (US); Brian R. Burroughs, Boston, MA (US); Daniel P. Hoeffel, Woodbury, MN (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/857,359

(22) Filed: Apr. 5, 2013

(65) Prior Publication Data
US 2013/0231751 A1 Sep. 5, 2013

Related U.S. Application Data

(60) Continuation of application No. 11/626,608, filed on Jan. 24, 2007, which is a division of application No. 10/144,762, filed on May 15, 2002, now Pat. No.
(Continued)

(51) Int. Cl.
*A61F 2/32* (2006.01)
*A61F 2/34* (2006.01)
(Continued)

(52) U.S. Cl.
CPC ... *A61F 2/34* (2013.01); *A61F 2/32* (2013.01); *A61F 2002/30382* (2013.01);
(Continued)

(58) Field of Classification Search
CPC .................................... A61F 2/32; A61F 2/34
USPC .............................................. 623/22.11–22.2
See application file for complete search history.

(56) References Cited

U.S. PATENT DOCUMENTS

| | | | |
|---|---|---|---|
| 3,297,641 | A | 1/1967 | Werber et al. |
| 3,352,818 | A | 11/1967 | Meyer et al. |

(Continued)

FOREIGN PATENT DOCUMENTS

| | | |
|---|---|---|
| EP | 0373800 B1 | 6/1990 |
| EP | 0722973 A1 | 7/1996 |

(Continued)

OTHER PUBLICATIONS

Atkinson, Silane Cross-Linked HDPE for Prosthetic Applications, Polymers in Med. and Surgery, Conf. Held by Plastics & Rubber Inst. & Biological Eng. Soc. (1989).

(Continued)

*Primary Examiner* — Jason-Dennis Stewart
(74) *Attorney, Agent, or Firm* — Perkins Coie LLP

(57) ABSTRACT

The present invention provides monopolar acetabular liners (32, 54) that can enclose a femoral head (14) to form a hip replacement prosthesis (30, 50), wherein the liner (32, 54) has a rim (34) that creates an orifice, wherein the orifice has a diameter that is smaller than the diameter of the femoral head (14), and wherein the liner (32, 54) encompasses greater than 50 percent of the volume of the head (14), wherein a constraining ring (56) can be used in conjunction with the monopolar constrained acetabular liner (32, 54) to provide additional support for the femoral head (14) to stay with the acetabular liner (32, 54) and avoid dislocation. Assemblies and complete prosthetic replacements are also provided. Liners (32, 54) and constraining rings (56) having no, one or more recesses (36) also are provided.

25 Claims, 4 Drawing Sheets

Related U.S. Application Data 7,169,186, which is a continuation of application No. PCT/US01/22638, filed on Jul. 19, 2001.

(60) Provisional application No. 60/289,528, filed on May 9, 2001, provisional application No. 60/234,345, filed on Sep. 22, 2000, provisional application No. 60/222,049, filed on Jul. 31, 2000.

(51) Int. Cl.
*A61L 27/16* (2006.01)
*A61F 2/30* (2006.01)
*A61F 2/36* (2006.01)
*A61F 2/46* (2006.01)

(52) U.S. Cl.
CPC ........... *A61F 2002/30433* (2013.01); *A61F 2002/3054* (2013.01); *A61F 2002/30604* (2013.01); *A61F 2002/30606* (2013.01); *A61F 2002/30685* (2013.01); *A61F 2002/3233* (2013.01); *A61F 2002/3241* (2013.01); *A61F 2002/3443* (2013.01); *A61F 2002/3446* (2013.01); *A61F 2002/3491* (2013.01); *A61F 2002/3493* (2013.01); *A61F 2002/3611* (2013.01); *A61F 2002/3625* (2013.01); *A61F 2002/4631* (2013.01); *A61F 2220/0033* (2013.01); *A61F 2220/0041* (2013.01); *A61F 2310/00017* (2013.01); *A61F 2310/00023* (2013.01); *A61F 2310/00029* (2013.01); *A61F 2310/00179* (2013.01); *A61L 27/16* (2013.01); *A61L 2430/24* (2013.01)

(56) References Cited

U.S. PATENT DOCUMENTS

| | | | |
|---|---|---|---|
| 3,758,273 A | 9/1973 | Johnston et al. | |
| 3,944,536 A | 3/1976 | Lupton et al. | |
| 4,380,090 A * | 4/1983 | Ramos | 623/22.2 |
| 4,535,486 A | 8/1985 | Roberts et al. | |
| 4,586,995 A | 5/1986 | Randall et al. | |
| 4,655,769 A | 4/1987 | Zachariades et al. | |
| 4,676,799 A | 6/1987 | Legrand | |
| 4,747,990 A | 5/1988 | Gaussens et al. | |
| 4,770,661 A * | 9/1988 | Oh | 623/22.2 |
| 4,892,552 A | 1/1990 | Ainsworth et al. | |
| 4,902,460 A | 2/1990 | Yagi et al. | |
| 4,944,974 A | 7/1990 | Zachariades | |
| 4,960,427 A | 10/1990 | Noiles | |
| 5,001,008 A | 3/1991 | Tokita et al. | |
| 5,001,206 A | 3/1991 | Bashir et al. | |
| 5,019,105 A | 5/1991 | Wiley | |
| 5,024,670 A | 6/1991 | Smith et al. | |
| 5,037,928 A | 8/1991 | Li et al. | |
| 5,059,196 A | 10/1991 | Coates | |
| 5,066,755 A | 11/1991 | Lemstra | |
| 5,123,924 A | 6/1992 | Sioshansi et al. | |
| 5,123,925 A | 6/1992 | Smestad et al. | |
| 5,160,464 A | 11/1992 | Ward et al. | |
| 5,160,472 A | 11/1992 | Zachariades | |
| 5,407,623 A | 4/1995 | Zachariades et al. | |
| 5,414,049 A | 5/1995 | Sun et al. | |
| 5,428,079 A | 6/1995 | Bastiaansen et al. | |
| 5,449,745 A | 9/1995 | Sun et al. | |
| 5,466,530 A | 11/1995 | England et al. | |
| 5,478,906 A | 12/1995 | Howard | |
| 5,480,683 A | 1/1996 | Chabrol et al. | |
| 5,515,590 A | 5/1996 | Pienkowski | |
| 5,543,471 A | 8/1996 | Sun et al. | |
| 5,549,698 A | 8/1996 | Averill et al. | |
| 5,549,700 A | 8/1996 | Graham et al. | |
| 5,593,719 A | 1/1997 | Dearnaley | |
| 5,650,485 A | 7/1997 | Sun et al. | |
| 5,684,124 A | 11/1997 | Howard et al. | |
| 5,725,591 A | 3/1998 | DeCarlo et al. | |
| 5,728,748 A | 3/1998 | Sun et al. | |
| 5,753,182 A | 5/1998 | Higgins | |
| 5,800,555 A | 9/1998 | Gray | |
| 5,824,411 A | 10/1998 | Shalaby et al. | |
| 5,879,400 A | 3/1999 | Merrill et al. | |
| 5,879,406 A * | 3/1999 | Lilley | 623/22.15 |
| 5,972,444 A | 10/1999 | Patel et al. | |
| 6,005,053 A | 12/1999 | Parikh et al. | |
| 6,017,975 A | 1/2000 | Saum et al. | |
| 6,093,208 A * | 7/2000 | Tian | 623/22.2 |
| 6,152,961 A | 11/2000 | Ostiguy, Jr. et al. | |
| 6,165,220 A | 12/2000 | McKellop et al. | |
| 6,168,626 B1 | 1/2001 | Hyon et al. | |
| 6,174,934 B1 | 1/2001 | Sun et al. | |
| 6,184,265 B1 | 2/2001 | Hamilton et al. | |
| 6,228,900 B1 | 5/2001 | Shen et al. | |
| 6,242,507 B1 | 6/2001 | Saum et al. | |
| 6,245,276 B1 | 6/2001 | McNulty | |
| 6,281,264 B1 | 8/2001 | Salovey et al. | |
| 6,316,158 B1 | 11/2001 | Saum et al. | |
| 6,464,926 B1 | 10/2002 | Merrill et al. | |
| 6,527,808 B1 | 3/2003 | Albertorio | |
| 6,641,617 B1 * | 11/2003 | Merrill et al. | 623/23.58 |
| 7,169,186 B2 | 1/2007 | Harris et al. | |
| 8,608,806 B2 | 12/2013 | Harris et al. | |
| 2007/0135927 A1 | 6/2007 | Harris et al. | |

FOREIGN PATENT DOCUMENTS

| | | |
|---|---|---|
| EP | 0729981 B1 | 9/1996 |
| EP | 0737481 A1 | 10/1996 |
| JP | 58157830 | 9/1983 |
| JP | 4198242 | 6/1992 |
| JP | 4185651 | 7/1992 |
| WO | WO98/01085 | 1/1998 |
| WO | WO01/05337 | 1/2001 |

OTHER PUBLICATIONS

Dijkstra et al., Polymer 30: 866-873 (1989).
Gielenz et al., Colloid & Polymer Sci. 260: 742-753 (1982).
Grobbelaar et al., J. of Bone and Joint Surgery 60-B(3): 370-374 (1978).
Grobbelaar et al., SA Bone and Joint Surgery IX(3): 143-147 (1999).
Jahan et al., J. of Biomed Research 25: 1005-1016 (1991).
Jahan et al., J. of Luminescence 40 & 41:242-243 (1988).
Kang et al., J. of Amer. Chem. Soc. 89(9): 1980-1986 (1967).
Nusbaum et al., J. of Boimed Material Research 13: 557-576 (1979).
Oonishi et al., Encyclopedic Handbook of Biomaterials and Bioengineering 2: 1853-1868 (1995).
Rose et al., J. of Orthopaedic Research Society 2(4): 393-400 (1984).
Saunders et al., Medical Device & Diagnostic Industry 222:89-92 (1993).
Streicher, Investigation on Sterilization and Modification of High Molecular Weight Polyethylenes by Ionizing Irradiation, Beta-Gamma (Jan. 1989).
Zoepfl et al., J. Polymer Sci Polym. Chem. Ed 22: 2017-2032 (1984).
Answer of Defendants Massachusetts Institute of Tech. and the General Hospital Corporation to Amended Complaint and Amended Counter Claim.
Reply of Plaintiff, Ambuj D. Sagar, Ph.D., to Amended Counterclaim of Def. Massachusetts Institute of Technology and the General Hospital Corp.
Long Term Performance of Gamma Irradiated HDPE Cups in Total Hip Replacement (1997) (Abstract).

* cited by examiner

Constraining Ring (56) in Different Orientations.

MONOPOLAR CONSTRAINED ACETABULAR COMPONENT

This application is a continuation of U.S. application Ser. No. 11/626,608 filed Jan. 24, 2007, which is a divisional of U.S. application Ser. No. 10/144,762 filed May 15, 2002, now U.S. Pat. No. 7,169,186, which is a continuation of PCT/US01/22638 filed Jul. 19, 2001, which claims benefit of U.S. Provisional No. 60/289,528 filed May 9, 2001, U.S. Provisional No. 60/234,345 filed Sep. 22, 2000, and U.S. Provisional No. 60/222,049 filed Jul. 31, 2000. The entire contents of the above-identified applications are hereby incorporated by reference.

The present invention relates to improved acetabular components, such as liners, assemblies and complete replacements, for use in the body. The improved acetabular components can be used, for example, in hip arthroplasties in both a primary and revision setting. The present invention provides a decreased risk of dislocation while facilitating greater range of motion ("ROM").

DESCRIPTION OF THE FIELD

Dislocation is a major source of morbidity at re-operation after total hip arthroplasty. Dislocation rates have been quoted at 1-10% for primary total hip arthroplasties. Many studies have shown increased rates of dislocation after revision total hip arthroplasty when compared with primary total hip arthroplasty. Currently, the chance of "successful surgical management of a recurrent dislocation" is 70% when a cause for the dislocation can be identified. Dislocation results in significant patient anxiety. In addition, the costs associated with surgical management of dislocation are significant.

A variety of approaches have been used to address dislocation, including changing the angle of the femoral component, changing the angle of the acetabular component, using extended lip liners, using off-set liners, advancing the greater trochanter, and using constrained acetabular components. Another approach is to use femoral heads of larger diameter.

Some of these approaches have distinct disadvantages, however. Altering the orientation of the components can increase stability in one direction (for example, posteriorly) but at the same time decrease stability in the opposite direction (for example, anteriorly). Use of extended lip liners and currently available constrained acetabular components which utilize additional polyethylene to surround the femoral head increases joint stability but this additional material also can, depending on the design, constrict the range of motion of the joint and can lead to subsequent problems related to impingement. When the hip joint is articulated (for example, flexed, extended, rotated, etc.) to its limit, impingement between the femoral neck and acetabular liner may occur.

Component impingement is undesirable for several reasons. The femoral neck impinging against the polyethylene liner can produce damage to the polyethylene as well as increasing the stresses at the component/bone interface. Additionally, the point of impingement acts as the fulcrum through which the force produced by the leg could lever the femoral head out of the liner and hence lead to dislocation.

Many current methods of reducing the risk of dislocation, including recurrent dislocation, employ the use of so called "constrained liners," which are complex bipolar or tripolar articulations. In a study of twenty one constrained acetabular components to treat preoperative or intraoperative instability, six patients had recurrent dislocations. It was postulated that this increase was caused by the impingement of the femoral stem on the rim of the insert due to decreased range of motion within the design. Orthopaedic Knowledge Update, Chapter 38, page 474 (James H. Beatty, M.D., editor, AAOS).

Constrained systems that are currently available use ultra high molecular weight polyethylene (UHMWPE) which is not crosslinked. A major limitation of the material is it's high wear rate and the risk of periprosthetic osteolysis. Also, their stated range of motion in flexion is between 72° and 90°. Such devices are available from Zimmer, Inc., Johnson & Johnson/Depuy Inc., and Howmedica-Osteonics, Inc.

The current products have additional limitations. For example, the Osteonics system utilizes only 22, 26 and 28 mm heads. The minimum diameter of the acetabular shell is 50 mm. This design is "bipolar." A bipolar system is made up of a acetabular shell with a polyethylene liner, and inside of that liner is a metal head. Inside of that metal head is another polyethylene liner, which in turn captures a 22, 26, or 28 mm head that is attached to the femoral stem. Thus, the Osteonics system has multiple polyethylene on metal articulations. The multiple articulations generate polyethylene wear debris at a much faster rate than designs with a single metal on polyethylene articulation. Additionally, the range of motion only is approximately 90 degrees.

A constrained system developed by Zimmer, Inc. uses a metal shell with a two-piece polyethylene liner. One piece is inserted into the acetabular metal shell followed by placement of the other portion around the neck on the femoral component before the femoral head has been put on the Morse taper. The head is then reduced into the acetabular component. The polyethylene portion with a metal band that is around the femoral neck is then brought into contact with the acetabular polyethylene component and the metal band then secured to "capture" the head within the assembled polyethylene liner. Again, this design uses ultra high molecular weight polyethylene and can generate significant debris as well as a limited range of motion. The limited range of motion results in impingement in flexion, which generates a rotational torque at the bone shell interface, potentially inhibiting bony in-growth into the acetabular shell.

In the late 1960's to early 1970's, others attempted to implant a cemented conventional UHMWPE liner with greater than 50% head coverage. Lagrange and Letournel, *Int Surg.* 60(1):21-4 (1975); Lanzetta, *Arch Ortop.* 83(1):49-53 (1970). These designs had a 35 mm inner diameter and was available in only two (47 and 58 mm) outer diameters. These approaches, however, did not yield a replacement with acceptable performance. Long-term data is not available for the LaGrange/Letournel design, likely because it did not become a widely-accepted product. Its head design (35 mm diameter) in conjunction with conventional UHMWPE available at the time would have had a substantial wear rate.

Thus, current and past designs have utilized various approaches, including countersinks, in which the center of rotation of the femoral head is below the level of the flat surface of the liner. Yet even the use of a countersink design using large head diameters is less than optimal because, among other things, these liners did not have an orifice that was less than the diameter of the femoral head, and therefore have no mechanical capture, and took no other steps to avoid or minimize dislocation.

It has been shown that larger heads are effective in reducing the rate of recurrent dislocations, even when used with conventional polyethylene. Amstutz et al., 12th Annual International Symposium for Technology in Arthroplasty, ISTA '99, Chicago, Ill. (1999). However, hip simulator studies have shown that the wear of conventional polyethylene with the larger heads is excessive. This disadvantage was demonstrated in vivo by the results of surface replacement as well.

Amstutz et al., *Clin. Orthop.* 213: 92-114 (1986). In addition, simply using a large head diameter does not produce mechanical capture of the femoral head.

In achieving some of the advantages of the invention, in accordance with one aspect of the invention, there are provided liners with one or more recesses. The type of recesses according to the present invention, however, are different than that of the unconstrained Modell St. Georg/Mark I & II and ENDO-Modell liner, which was to "prevent irritation of the psoas muscle and enable(s) removal of cement," rather than for reducing dislocation or impingement. See Englelbrechht E, Siegel A, Kluber D: The Modell St. Georg/Mark I/Mark II Prosthesis. p. 66. In: Finerman G, Dorey F, Grigoris P, McKellop H (eds): Total Hip Arthroplasty Outcomes. Churchhill Livingstone, N.Y., 1998.

In view of the limitations of the commercialized designs, new approaches are needed that would increase the inherent stability of the head-liner articulation while at the same time increasing range of motion, which would result in a decreased rate of dislocation for both primary and revision total hip arthroplasties. Such approaches would decrease patient anxiety, eliminate the need for postoperative dislocation precautions, and reduce the number of revisions performed for dislocation and recurrent dislocation resulting in a net cost savings to the healthcare system. Such risks of dislocation are markedly reduced while range of motion is increased, particularly when a large-head design and/or recesses are employed.

Cut away monopolar constrained acetabular liners (U.S. Ser. Nos. 60/222,049 and 60/234,345) for use in total hip replacement to help reduce the potential of dislocation of the hip while still providing sufficient range of motion for daily activities have been developed. The invention disclosed herein also provides a separate constraining ring that can be used in conjunction with the monopolar constrained acetabular liner and the cut away monopolar constrained acetabular liner to provide additional support for the femoral head to stay with the acetabular liner and avoid dislocation.

SUMMARY OF THE INVENTION

It is an object of the invention to provide improved prostheses for use in the hip. In accomplishing this and other objects, there is provided in accordance with one aspect of the present invention a monopolar acetabular liner that can enclose a femoral head to form a hip replacement prostheses, wherein the liner has a rim that creates an orifice, and wherein the orifice has a diameter that is smaller than the diameter of the femoral head. The rim extends beyond the center line of the head (such as the center of rotation) when the head is enclosed by the liner, and thereby the head is constrained from dislocation. The liner can, in certain embodiments, include one or more recesses or cut-aways to facilitate additional range of motion or be without recess or cut away for use with liners that likewise lack a recess or cut away. The liner, in another embodiment, is designed to accommodate proper fitting of a constraining ring that can be used in conjunction with the monopolar constrained acetabular liner and the cut away monopolar constrained acetabular liner. In accordance with another embodiment, there is provided a constraining ring that can be used in conjunction with the monopolar constrained acetabular liner and the cut away monopolar constrained acetabular liner. The constraining rings provide additional support for the femoral head to stay with the acetabular liner and avoid dislocation. Preferably, the liner comprises ultra high molecular weight polyethylene, that more preferably is all or in part cross-linked. Preferably, the cross-linking is performed via irradiation. The femoral head can have a large diameter. The constraining ring can, in certain embodiments, include one or more recesses or cut-aways to be compatible with the corresponding liner. Alternatively, the constraining ring will be without a recess or cut away for use with liners that likewise lack a recess or cut away.

In accordance with another aspect of the present invention, there is provided a monopolar acetabular assembly comprising (A) a monopolar acetabular component that encloses a femoral head, wherein the liner has a rim that creates an orifice, and wherein the orifice has a diameter that is smaller than the diameter of the femoral head; and (B) a metal shell. The rim extends beyond the center line of the head (such as the center of rotation) when the head is enclosed by the liner, and thereby the head is constrained from dislocation. The liner can, in certain embodiments, include one or more recesses or cut-aways to facilitate additional range of motion or be without recess or cut away; and a constraining ring which can be used in conjunction with the monopolar constrained acetabular liner and the cut away monopolar constrained acetabular liner to provide additional support for the femoral head to stay with the acetabular liner and avoid dislocation. The constraining ring, which can be made from a number of high strength materials (for example, cobalt chrome alloy, titanium, stainless steel, etc.), is designed to fit around the perimeter of the liner. The constraining ring, in another embodiment, is designed to fit properly in conjunction with the monopolar constrained acetabular liner and the cut away monopolar constrained acetabular liner. Preferably, the liner comprises ultra high molecular weight polyethylene, that preferably is all or in part cross-linked. Preferably, the cross-linking is performed via irradiation. Preferably, the femoral head has a large diameter. The constraining ring can, in certain embodiments, include one or more recesses or cut-aways to be compatible with the corresponding liner. Alternatively, the constraining ring will be without a recess or cut away for use with liners that likewise lack a recess or cut away. In accordance with the invention, the constraining ring is preferably made of high strength materials such as cobalt chrome alloy, titanium, or stainless steel.

In accordance with still another aspect of the present invention, there is provided a hip joint replacement assembly comprising (A) a monopolar acetabular liner that encloses a femoral head, wherein the liner has a rim that creates an orifice, and wherein the orifice has a diameter that is smaller than the diameter of the femoral head; (B) a metal shell; and (C) a femoral head. The rim extends beyond the center line of the head (such as the center of rotation) when the head is enclosed by the liner, and thereby the head is constrained from dislocation. The liner can, in certain embodiments, include one or more recesses or cut-aways to facilitate additional range of motion or be without recess or cut away; and a constraining ring which can be used in conjunction with the monopolar constrained acetabular liner and the cut away monopolar constrained acetabular liner to provide additional support for the femoral head to stay with the acetabular liner and avoid dislocation. The constraining ring, in another embodiment, is designed to fit properly in conjunction with the monopolar constrained acetabular liner and the cut away monopolar constrained acetabular liner. Preferably, the liner comprises ultra high molecular weight polyethylene, that preferably is all or in part cross-linked. Preferably, the cross-linking is performed via irradiation. The metal shell may be made of titanium, stainless steel, or a cobalt chrome alloy. Preferably, the femoral head has a large diameter. The constraining ring can, in certain embodiments, include one or more recesses or cut-aways to be compatible with the corresponding liner.

Alternatively, the constraining ring will be without a recess or cut away for use with liners that likewise lack a recess or cut away.

In accordance with the invention, metal shells preferably are made of titanium, cobalt chrome alloys, or stainless steel. The femoral stems preferably also may be made of a cobalt chrome alloys, stainless steel, or titanium. Preferably, the femoral heads are made of a cobalt chrome alloys, stainless steel or ceramic. Where the femoral head and stem are one piece, preferably they are made of a cobalt chrome alloy or stainless steel.

In accordance with still a further aspect of the invention, there are provided methods of replacing a hips in patients in need thereof, comprising the step of surgically implanting in a given patient a monopolar acetabular liner that can enclose a femoral head to form a hip replacement prostheses, wherein the liner has a rim that creates an orifice, and wherein the orifice has a diameter that is smaller than the diameter of the femoral head, and thereby the head is constrained from dislocation. The liner can, in certain embodiments, include one or more recesses or cut-aways to facilitate additional range of motion or be without recess or cut away; and a constraining ring which can be used in conjunction with the monopolar constrained acetabular liner and the cut away monopolar constrained acetabular liner to provide additional support for the femoral head to stay with the acetabular liner and avoid dislocation. The constraining ring, in another embodiment, is designed to fit properly in conjunction with the monopolar constrained acetabular liner and the cut away monopolar constrained acetabular liner. Implantation of assemblies and total replacements, such as shells, femoral heads and femoral stems, also are provided.

In contrast to current bipolar and tripolar constrained components the monopolar constrained design has: (i) increased range of motion, (ii) decreased wear of the articulation, (iii) simpler intraoperative assembly, (iv) decreased risk of impingement of the femoral neck upon the liner rim, (v) decreased stress transfer to the acetabular component-cement interface, (vi) decreased stress transfer to the cement-bone interface, (vii) decreased stress transfer to the metal shell-bone interface, (viii) eliminates the thin polyethylene articulating surfaces associated with multi-polar designs, (ix) eliminates multipolar locking rings, which have had reported malfunctions and failure, (x) allows for the use of large head diameters, (xi) has smaller possible acetabular shell outer diameters, (xii) utilizes thicker polyethylene bearing surfaces, (xiii) and further facilitate range of motion in preferred directions.

In contrast to the Legrange/Letournel design, the monopolar constrained design according to the invention has: (i) a different and superior bearing surface, (ii) larger head diameters, (iii) decreased wear, (iv) increased ROM, (v) the capacity to be use in cemented or bony in-growth acetabular replacements, (vi) thicker polyethylene bearing surfaces, (vii) modularity for use with uncemented acetabular shells, (viii) can be easily exchanged at the time of primary or revision surgery, and (ix) and can be designed to facilitate movement in preferred directions.

Although large head diameters with standard UHMWPE bearing surfaces have been used for the treatment of dislocation and recurrent dislocation by Amstutz et al. In contrast to the designs employed by Amstutz, the monopolar constrained has: (i) has a mechanical capture of the femoral head, (ii) reduced wear, (iii) decreased periprosthetic osteolysis, (iv) modularity for easy conversion between different amounts of constraint, and (v) can be designed to facilitate movement in preferred directions.

In embodiments employing the recesses, the liner can have one or more recess. A recess, often referred to herein as a cut away, can be positioned to further facilitate movement in a desired direction.

Embodiments employing a constraining ring can be used in conjunction with the monopolar constrained acetabular liner and the cut away monopolar constrained acetabular liner to provide addition restraint against dislocation of the hip joint while at same time not impeding the range of motion of the hip joint. The constraining ring, in another embodiment, is designed to fit properly in conjunction with the monopolar constrained acetabular liner and the cut away monopolar constrained acetabular liner.

The constraining ring can be secured to the acetabular liner by means of a number of locking mechanisms that are similar to those that are currently used to secure acetabular liners into their mating metal acetabular shell. Embodiments of this invention have used a locking mechanism which relies on the spatial interference between the polyethylene acetabular liner and the metal acetabular shell. This invention is not limited by the use of the locking mechanism used in such embodiments and the use of other locking mechanisms are possible.

In another embodiment of this invention have used a locking mechanism which relies on the spatial interference between the polyethylene acetabular liner and the metal constraining ring. As the constraining ring is being seated onto the acetabular liner the polyethylene must deform as it moves past a ridge on the constraining ring. Once the ring is fully seated then the deformed polyethylene relaxes behind the ridge hence securing the constraining ring to the liner. This invention is not limited by the use of the locking mechanism used in such embodiments and the use of other locking mechanisms are possible. Yet in another the constraining ring can also be fastened to the acetabular liner by direct screw fixation where screws are passed directly through the constraining ring into the polyethylene liner.

In another embodiment of this invention the constraining ring can be secured to the liner by means of a retaining ring which is designed in an unstressed state to sit in grooves in both the constraining ring and acetabular liner. Upon setting the constraining ring onto the liner the retaining will deform until the constraining ring is fully seated onto the liner at which point the retaining ring relaxes into the designed grove in the liner.

The constraining ring can, in certain embodiments, include one or more recesses or cut aways to be compatible with the corresponding liner. Alternatively, the constraining ring will be without a recess or cut away for use with liners that likewise lack a recess or cut away.

These and other aspects of the present invention will become apparent to the skilled person in view of the description set forth below.

DETAILED DESCRIPTION OF ASPECTS OF THE INVENTION

Figure 1:
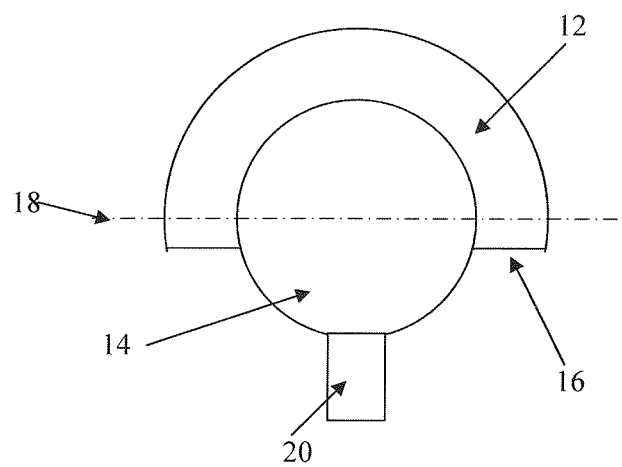
FIG. 1 is a schematic view of a monopolar liner in functional relation with a femoral head and neck.

The present invention decreases the risk of dislocation of total hip arthroplasty in both the primary and revision setting. See U.S. Ser. No. 60/222,049, filed Jul. 31, 2000, and U.S. Ser. No. 60/234,345, filed Sep. 22, 2000, the entirety of which are hereby incorporated by reference. In conjunction with large diameter femoral heads, such as disclosed in PCT/US99/16070 (the entirety of which is hereby incorporated by reference), the present invention can achieve a range of motion that is greater than is currently available so called "constrained" systems using 22, 26, 28 and 32 mm heads. A decrease in the rate of dislocation will have a positive effect on patient satisfaction as well as hospital re-admission for treatment of dislocation. The increased range of motion in this invention will afford patients a more normal life style than the currently available constrained systems. The present invention can be surgically implanted in a patient in the same or similar manner as currently employed implants. Thus, the present invention results in an improved quality of life as well as improved patient satisfaction.

The present invention advantageously employs UHMWPE liners, preferably using UHMWPE that is cross-linked, including highly cross-linked UHMWPE. UHMWPE can be cross-linked by a variety of approaches, including those employing cross-linking chemicals and/or irradiation. Preferred approaches for cross-linking employ irradiation, and are taught in PCT/US97/02220, the entirety of which is hereby incorporated by reference.

According to the invention, there is preferably a two part acetabular assembly, namely a metal shell for bony in-growth with UHMWPE liner, preferably where the bearing surface of the liner that comes into contact with the femoral head is comprised of crosslinked UHMWPE.

The liner of the present invention preferably is "monopolar" system. The monopolar constrained acetabular preferably has a one piece design and has a single metal to polyethylene articular surface, and thus preferably is not bipolar or tripolar in design. The monopolar design allows for the use of thicker polyethylene in the acetabular liner. Compared to the bipolar and tripolar constrained/captured designs, the monopolar design decreases the surface area of contact between metal and polyethylene because there is only one metal-polyethylene articulation, rather than two or more found in other designs. Moreover, the use of crosslinked UHMWPE will decrease the amount of debris particles generated to articulation. Moreover, in the modular form of this acetabular design, since the polyethylene component is not cemented into place, some revision surgeries are more feasible. Moreover, with the modular design different types of heads and liners can be used with the shell, and can be selected by the surgeon during surgery.

According to one aspect of the invention, more than 50% of the volume of the femoral head is enclosed within the polyethylene liner. The diameter of the opening/orifice of the polyethylene liner is less than the diameter of the femoral head that is inserted, as shown in FIG. 1.

FIG. 1 depicts at (10) a liner (12) in functional relation with a femoral head (14) and neck (20). The rim surface (16) of the liner (12) extends beyond the center line (18), representing the center of rotation of both the femoral head and the acetabular liner. Preferably the liner rim surface is flat in this embodiment. The inner portions of the rim circumscribe the orifice. If desired, a metal shell, not pictured, would be positioned between the liner and the bone at the mount site, and preferably is configured so as to promote in-growth of the bone.

Figure 2:
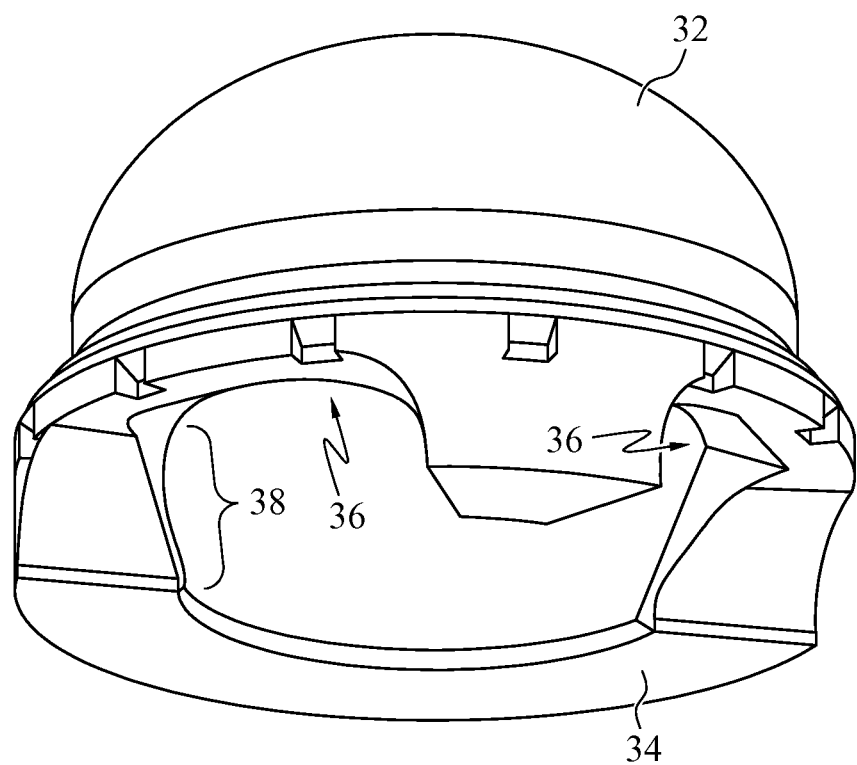
FIG. 2 is a perspective view of a monopolar liner containing 2 recesses to facilitate greater range of motion.

FIG. 2 depicts at (30) a type of recessed or cut away liner (32). In the pictured embodiment, the rim surface (34) is interrupted by two cut aways (36) which permit greater range of motion while preserving a constraint to hold a head in place by a snap fit. Region (38) shows that the rim surface (34) of the liner (32) extends beyond the center line (not specifically depicted) in such a manner that the opening/orifice of the liner (32) is less than the diameter of the femoral head that is inserted therein. Thus, the inner portions of the rim circumscribe the orifice in such a manner that the head is held within the liner. If desired, a metal shell, not pictured, would be positioned between the liner and the bone at the mount site, and preferably is configured so as to promote in-growth of the bone.

The embodiments that employ one or more recesses can have the recesses positioned to further facilitate movement in a desired direction. For example, a liner might have a single recess to provide increased range of motion in flexion. Another arrangement can be a liner with two recesses with the second recess to provide increased range of motion in extension and/or extension plus external rotation. Moreover, the increased range of motion provided by the cut-away design also allows for greater tolerance for the variations in the orientation of the acetabular component that can occur during insertion.

As stated above, recesses can be positioned to further facilitate movement in a desired direction, such as in the common directions of impingement. Recesses can be placed in several different positions, but preferentially would be placed in the position to produce the range of maximum motion in a desired direction. For example, in a left hip, when looking at the acetabular component in position and considering it to be the face of a clock, the recess would be preferentially placed at about 1-2 o'clock. Under similar circumstances one would place a recess for a right hip at about 10-11 o'clock. Recesses in these positions assist with flexion alone and flexion plus internal rotation. For embodiments with two or more recesses, at least one recess also would be placed in the position to maximize extension alone and extension plus external rotation, and thus these recesses would be placed at about 4-5 o'clock in the left hip and about 7-8 o'clock in the right hip.

The recesses preferably are of sufficient size to accommodate the femoral head and stem (including the neck), while still constraining the head within the liner. The size of the recess in terms of width and depth depend upon the size of the stem neck and the range of motion of motion sought, which are readily determinable by the skilled person based upon a patient's size, age and needs. If the liner is comprised of a cross-linked polymer, like irradiated ultra high molecular weight polyethylene, then the recesses preferably are machined into the liner. The liner, in another embodiment, is modified to accommodate a constraining ring that can be used in conjunction with the monopolar constrained acetabular liner and the cut away monopolar constrained acetabular liner to provide additional support for the femoral head to stay with the acetabular liner and avoid dislocation.

Figure 3:
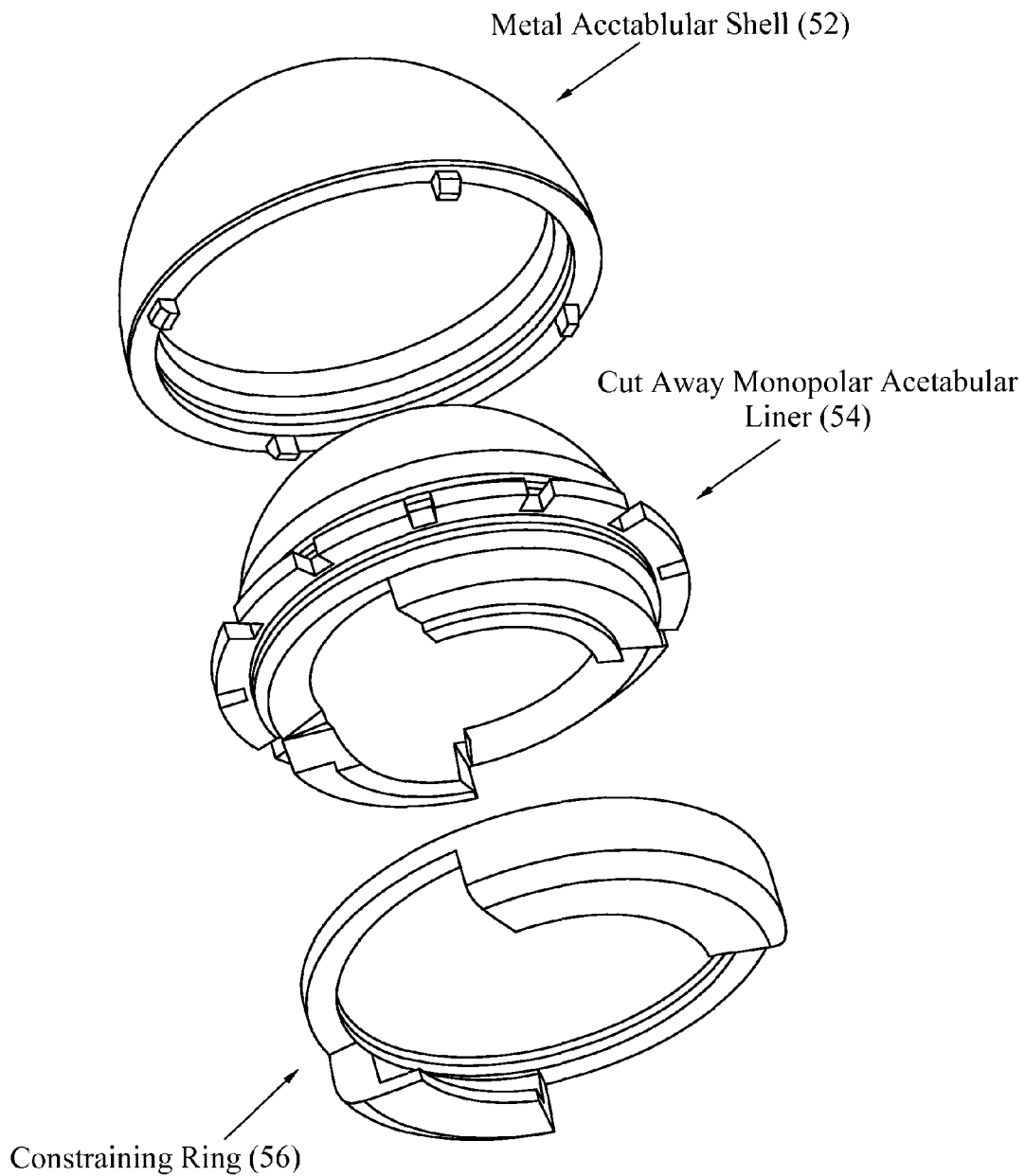
FIG. 3 depicts the components of the cut away monopolar constrained acetabular system with a constraining ring: metal acetabular shell (52) which is secured to the acetabulum, polyethylene cut away monopolar constrained acetabular liner (54), and constraining ring (56). Note the metal acetabular shell is not essential for this invention as the acetabular liner can be directed secured into the acetabulum with bone cement.

FIG. 3 depicts at (50) a type of constraining ring (56). In the pictured embodiment, showing components of the cut away monopolar constrained acetabular system with a constraining ring: optional metal acetabular shell which is secured to the acetabulum (52), polyethylene cut away monopolar constrained acetabular liner (54), and the constraining ring (56).

It is notable that the metal acetabular shell is not essential for this invention as the acetabular liner can be directed secured into the acetabulum with bone cement. If desired, the metal shell (52), would be positioned between the liner and the bone at the mount site, and preferably is configured so as to promote in-growth of the bone.

Figure 4:
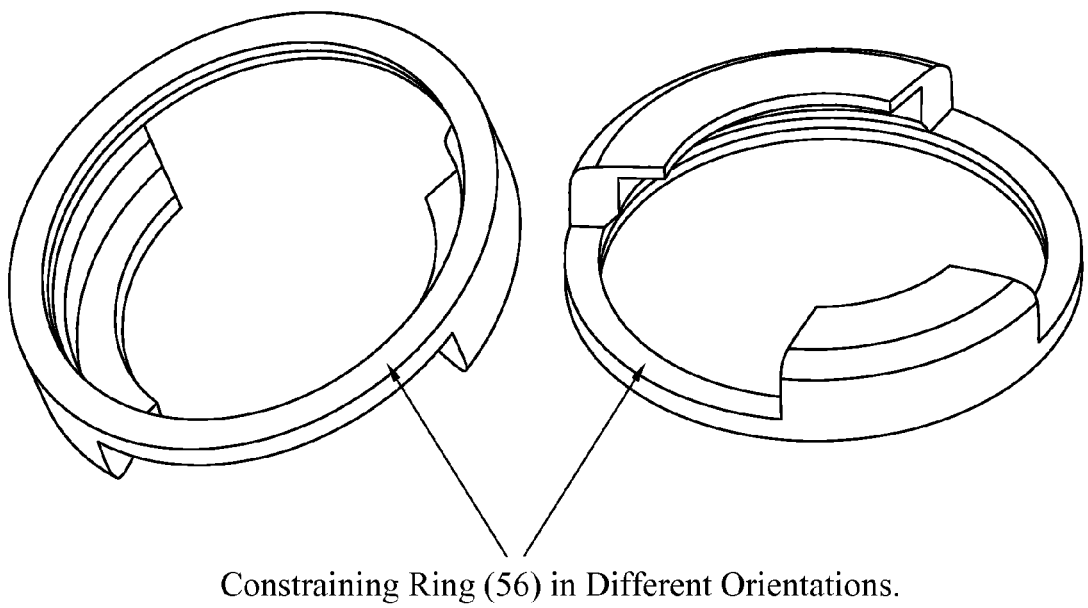
FIG. 4 depicts constraining rings (56) in different perspectives.

FIG. 4 depicts at (70) a constraining ring (56) shown in different perspectives.

The opening in the monopolar constrained acetabular liner and the cut away monopolar constrained acetabular liner through which the femoral head passes upon reducing the femoral head into the liner is smaller than the femoral head, which allows a snap-fit. Therefore, the constrained liner, which is typically made of polyethylene, must deform slightly to allow the femoral head to be embraced by the liner. The constraining ring, which can be made from a number of high strength materials (for example, cobalt chrome alloy, titanium, stainless steel, etc.), is designed to fit around the perimeter of the monopolar constraining acetabular liner and is intended to serve as a structural support of the liner to further ensure that the femoral head will stay within the acetabular liner.

The constraining ring is circular in shape and has "cutouts" similar to that of the cut away monopolar constrained acetabular liner (FIGS. 3 & 4). This prevents the constraining ring from interfering with the range of motion of the hip.

The constraining ring is preferably designed to be a single piece which can be set onto the acetabular liner during the operative procedure after the femoral head has been snap-fitted into the acetabular liner. This allows for the femoral head to stay snapped within the constrained liner.

The constraining ring can, in certain embodiments, include one or more recesses or cut-aways to be compatible with the corresponding liner. Alternatively, the constraining ring will be without a recess or cut away for use with liners that likewise lack a recess or cut away.

Gross sliding or micro motion between separate metallic surfaces of the total hip components can generate wear debris which upon release into the joint space can elicit a biological response that can lead to the development of osteolysis and hence increasing the of potential of component loosening. The design of the constraining ring and the acetabular liner are such that to prevent contact between metallic surfaces. The constraining ring is designed to fit properly in conjunction with the monopolar constrained acetabular liner and the cut away monopolar constrained acetabular liner.

The components are designed such that the femoral neck will impinge against the polyethylene liner and not the metallic constraining ring in all directions of motion. Also, the constraining ring fastens directly to the polyethylene acetabular liner and has no direct contact with the metal shell into which the liner is set. Another advantage to this feature is that the use of the constraining ring is not dependent on the use of a metal shell, hence allowing this system to be used with an acetabular liner which is cemented directly into the acetabulum.

The constraining ring (see FIGS. 3 & 4) can be secured to the acetabular liner by means of a number of locking mechanisms which are currently used to secure acetabular liners into their mating metal acetabular shell. Embodiments of this invention have used a locking mechanism which relies on the spatial interference between the polyethylene acetabular liner and the metal acetabular shell. This invention is not limited by the use of the locking mechanism used in such embodiments and the use of other locking mechanisms are possible.

In another embodiment of this invention have used a locking mechanism which relies on the spatial interference between the polyethylene acetabular liner and the metal constraining ring. As the constraining ring is being seated onto the acetabular liner the polyethylene must deform as it moves past a ridge on the constraining ring. Once the ring is fully seated then the deformed polyethylene relaxes behind the ridge hence securing the constraining ring to the liner. This invention is not limited by the use of the locking mechanism used in such embodiments and the use of other locking mechanisms are possible and contemplated by the invention.

Yet in another the constraining ring can also be fastened to the acetabular liner by direct screw fixation where screws are passed directly through the constraining ring into the polyethylene liner.

In another embodiment of this invention the constraining ring can be secured to the liner by means of a retaining ring which is designed in an unstressed state to sit in grooves in both the constraining ring and acetabular liner. Upon setting the constraining ring onto the liner the retaining will deform until the constraining ring is fully seated onto the liner at which point the retaining ring relaxes into the designed grove in the liner.

The constraining ring can, in certain embodiments, include one or more recesses or cut-aways to be compatible with the corresponding liner. Alternatively, the constraining ring will be without a recess or cut away for use with liners that likewise lack a recess or cut away.

Description of the Assembly of Cut Away Monopolar Constrained Acetabular Liner with Constraining Ring (see FIG. 3):

Components of the cut away monopolar constrained acetabular system consisting of: i) metal acetabular shell which is secured to the acetabulum, ii) polyethylene cut away monopolar constrained acetabular liner, and iii) constraining ring. The metal acetabular shell is not essential for this invention as the acetabular liner can be directed secured into the acetabulum with bone cement. The cut away monopolar constrained acetabular liner is set into the metal acetabular. The constraining ring is placed over the femoral component and the femoral head is snap-fitted into the acetabular liner. The constraining ring is then set onto the cut away monopolar constraining acetabular liner with the cutouts of the constraining ring aligned with the cutouts of the acetabular liner.

Demonstration of the Position of the Acetabular Component within the Hip and Range of Motion:

The actual position of the acetabular component within the hip will be set during the operative procedure and will depend on the patient's anatomy and gait. The cut away portion of the acetabular component allows for sufficient range of motion in flexion. The cut away portion of the acetabular component allows for sufficient internal rotation at 90° of flexion. The cut away portion of the acetabular component allows for sufficient external rotation at neutral flexion.

In any of the embodiments of the invention, the liners of the invention can be used with hemispherical and non-hemispherical acetabular shells.

Also, the invention can be used with any head diameter, including large head diameters (for example, 35 mm or greater, such as 38 mm, 40 mm, 42 mm, 44 mm, and any diameter in between or larger) in order to increase the range of motion in comparison with currently available constrained systems.

The invention is further demonstrated by the following example, which do not limit the invention in any manner.

Example 1

The load required for insertion and dislocation of femoral heads in a constrained liner according to the invention was quantified by inserting 32 and 38 mm heads into simulated liners of electron beam crosslinked UHMWPE. Two and three dimensional modeling was performed to assess ROM and stability in vitro. The liner had no chamfer.

The ROM, and the loads required for insertion and dislocation using different opening diameters for 32 mm and 38 mm heads in simulated monopolar liners were measured. A 32 mm head with a 31 mm liner opening required 60 lbs. for insertion and 55 lbs. for dislocation. When the opening was increased to 31.5 mm the forces for insertion and dislocation decreased to 29 lbs., and 24 lbs., respectively. Testing of 35.5 mm, 36.5 mm, and 37.5 mm openings with a 38 mm head was performed. The insertional loads were 157, 130, and 28 lbs. The force necessary to produce dislocation of the femoral head were 135, 126, and 28 lbs., respectively.

The ROM for the 38 mm head and a 35.5 mm orifice liner is 110°. This increases to 118° and 131° as the orifice diameter is increased to 36.5 and 37.5 mm. The 32 mm head and 31 mm orifice liner has 116° ROM. The ROM increases to 124° when a 31.5 mm orifice is used with the 32 mm head.

These data demonstrate that the constrained design according to the invention can minimize the occurrence of dislocation, even with heads and liners that are constructed to permit enhanced range of movement.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

The invention claimed is:

1. A metallic constraining ring that fastens directly to a cut-away monopolar constrained acetabular liner, wherein the constraining ring has at least one positioned recess that is compatible with at least one recess on the cut-away monopolar constrained acetabular liner that comprises cross-linked ultrahigh molecular weight polyethylene, wherein the metallic constraining ring fits around the perimeter of the cut-away monopolar constrained acetabular liner, and wherein the metallic constraining ring is set onto the cut-away monopolar constrained acetabular liner during the operative procedure after the femoral head is reduced into the cut-away monopolar constrained acetabular liner, wherein following the operative procedure the metallic constraining ring is not impinged by a femoral neck, wherein at least one recess can be positioned to increase range of motion.

2. The metallic constraining ring according to claim 1, wherein the shape of the metallic constraining ring is circular.

3. The metallic constraining ring according to claim 1, wherein metallic constraining ring is made of at least one selected from the group consisting of cobalt chrome alloy, titanium, and stainless steel.

4. The metallic constraining ring according to claim 1, wherein the ring is a single piece.

5. The metallic constraining ring according to claim 1, wherein the metallic constraining ring has at least two recesses that are compatible with at least two respective recesses on the cut-away monopolar constrained acetabular liner, wherein the first recess of the metallic constraining ring increases flexion and the second recess of the metallic constraining ring increases extension.

6. A hip joint replacement assembly comprising:
(a) a monopolar constrained acetabular liner for enclosing a femoral head, wherein the liner has a rim that creates an orifice, wherein the orifice has a diameter that is smaller than the diameter of the femoral head, wherein the femoral head has a diameter of 32 mm or larger, wherein the monopolar constrained acetabular liner comprises cross-linked ultrahigh molecular weight polyethylene;
(b) a metallic constraining ring that fastens directly to the monopolar constrained acetabular liner and fits around the perimeter of the monopolar constrained acetabular liner, wherein the metallic constraining ring is capable of being set onto the acetabular liner during an operative procedure after the femoral head has been reduced into the monopolar constrained acetabular; and
(c) a femoral head attached to a femoral neck, wherein during movement the femoral neck can impinge upon the monopolar constrained acetabular liner and not the metallic constraining ring.

7. The hip joint assembly according to claim 6, wherein the metallic constraining ring can be used without a metal shell, thereby allowing the monopolar constrained acetabular liner to be cemented directly into the acetabulum.

8. The hip joint assembly according to claim 6, wherein the metallic constraining ring can be secured to the acetabular liner by at least one locking mechanism.

9. The hip joint assembly according to claim 6, wherein the shape of the metallic constraining ring is circular.

10. The hip joint assembly according to claim 6, wherein the metallic constraining ring is made of at least one selected from the group consisting of cobalt chrome alloy, titanium, and stainless steel.

11. The hip joint assembly according to claim 6, wherein the metallic constraining ring is a single piece.

12. The hip joint assembly according to claim 6, wherein the monopolar constrained acetabular liner is a cut away monopolar constrained acetabular liner.

13. The hip joint assembly according to claim 6, wherein the metallic constraining ring has no recess.

14. The hip joint assembly according to claim 6, wherein the metallic constraining ring has at least one recess.

15. The hip joint assembly according to claim 6, wherein the metallic constraining ring has at least two recesses.

16. The hip joint assembly according to claim 6, wherein the liner has no recess.

17. The hip joint assembly according to claim 6, wherein the liner is a cut-away liner that has at least one recess.

18. The hip joint assembly according to claim 6, wherein the liner is a cut-away liner that has at least two recesses.

19. A hip joint replacement assembly comprising:
(a) a cut-away monopolar constrained acetabular liner for enclosing a femoral head, wherein the cut-away monopolar constrained acetabular liner comprises cross-linked ultrahigh molecular weight polyethylene, and has
 (i) a rim that creates an orifice that has a diameter that is smaller than the diameter of the femoral head, and
 (ii) at least one recess;
(b) a metallic constraining ring that fastens directly to the monopolar constrained acetabular liner and fits around the perimeter of the cut-away monopolar constrained acetabular liner and has a recess that is compatible with the recess on the cut-away monopolar constrained acetabular liner; and
(c) a femoral head attached to a femoral neck, wherein during movement the femoral neck can impinge upon the monopolar constrained acetabular liner and not the metallic constraining ring.

20. The hip joint replacement assembly of claim 19, wherein the cut-away monopolar constrained acetabular liner has first and second recesses and the metallic constraining ring has first and second recesses that are respectively compatible with the first and second recesses on the cut-away monopolar constrained acetabular liner.

21. The hip joint replacement assembly of claim 20, wherein the first recesses on the cut-away monopolar constrained acetabular liner and the metallic constraining ring assist with flexion and the second recesses on the cut-away monopolar constrained acetabular liner and the metallic constraining ring maximize extension.

22. The hip joint replacement assembly of claim 21, wherein the first compatible recesses increase flexion and the second compatible recesses increase extension.

23. The hip joint replacement assembly of claim 19, wherein the femoral head has a diameter of at least 32 mm.

24. The hip joint replacement assembly of claim 23, wherein the femoral head has a diameter greater than 32 mm.

25. The hip joint assembly according to claim 19, wherein the metallic constraining ring is made of at least one selected from the group consisting of cobalt chrome alloy, titanium, and stainless steel.

* * * * *